United States Patent [19]

Herrin

[11] Patent Number: 5,308,345
[45] Date of Patent: May 3, 1994

[54] SYSTEM AND METHOD FOR MANUFACTURING DISPOSABLE DIAPERS HAVING ELASTIC WAISTBAND

[75] Inventor: Robert M. Herrin, Orlando, Fla.

[73] Assignee: John M. Tharpe, Albany, Ga. ; a part interest

[21] Appl. No.: 442,215

[22] Filed: Nov. 28, 1989

[51] Int. Cl.⁵ ............................................. A61F 13/15
[52] U.S. Cl. ................... 604/385.2; 156/164; 156/229; 156/496
[58] Field of Search ................. 604/358, 385.1, 385.2; 156/164, 229, 494, 495, 496

[56] References Cited

U.S. PATENT DOCUMENTS

| | | | |
|---|---|---|---|
| 2,429,177 | 10/1947 | Young | 156/164 |
| 2,434,111 | 1/1948 | Hawley, Jr. et al. | 156/164 |
| 4,284,454 | 8/1981 | Joa | 156/229 |
| 4,285,747 | 8/1981 | Rega | 156/164 |
| 4,405,397 | 9/1983 | Teed | 604/385.2 |
| 4,523,969 | 6/1985 | Spencer | 156/164 |
| 4,642,151 | 2/1987 | Coenen | 156/164 |
| 4,735,673 | 4/1988 | Piron | 156/496 |
| 4,925,520 | 5/1990 | Beaudoin et al. | 156/229 |
| 4,943,340 | 7/1990 | Vjimoto et al. | 156/229 |

*Primary Examiner*—Randall L. Green
*Assistant Examiner*—K. M. Reichle
*Attorney, Agent, or Firm*—Allen, Dyer, Doppelt, Franjola & Mildrath

[57] ABSTRACT

Disposable diapers are manufactured in a high-speed process with an elastic waistband formed of a stretched length of foam having an elastic memory by longitudinally stretching the elastic waistband length by gripping without penetrating at least one of its ends and fixing the stretched elastic waistband to the diaper layer along the waistband area. The end of the waistband length is positively engaged in a groove on a roller surface with a continuous belt which moves across the grooved roller surface and pinches without penetrating the end of the elastic foam length.

32 Claims, 4 Drawing Sheets

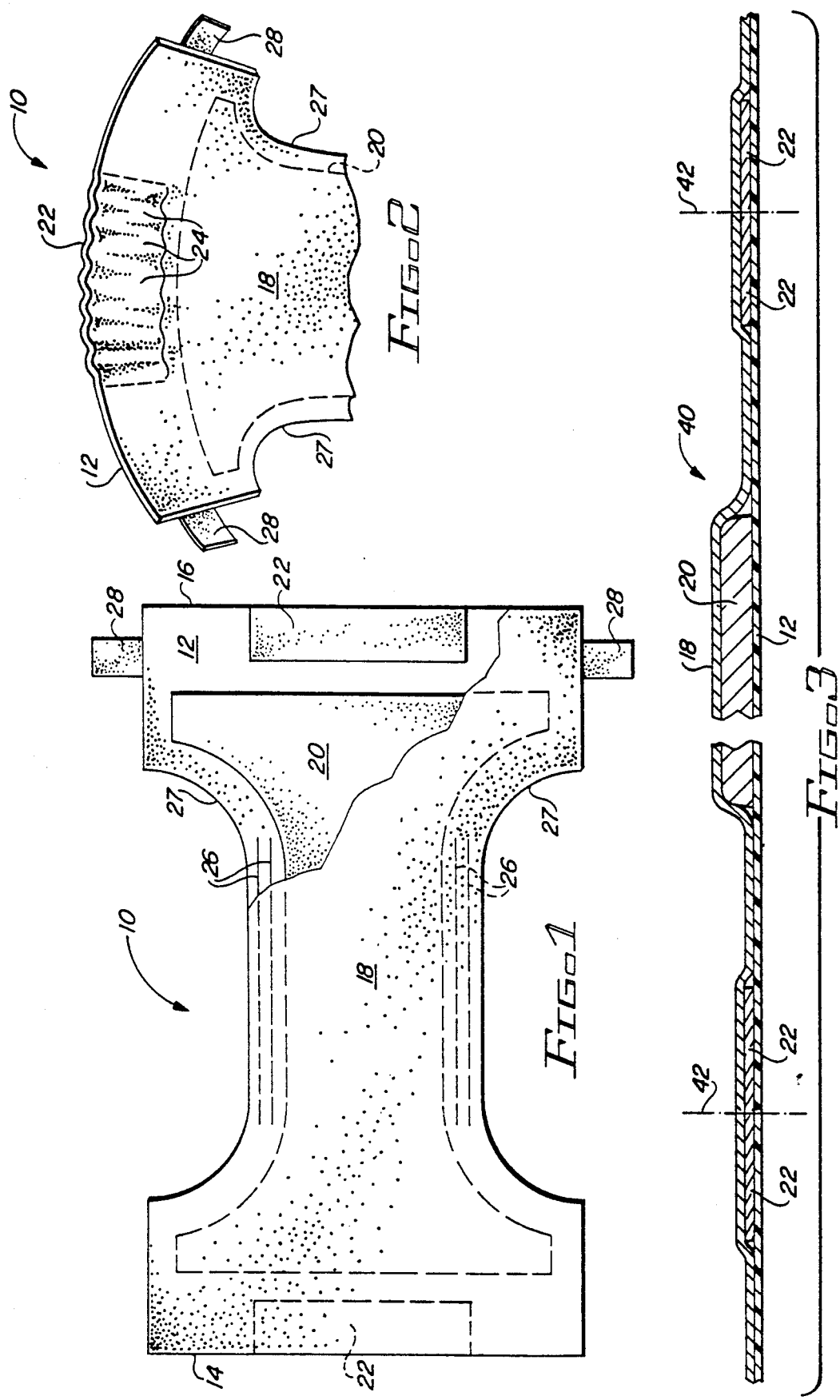

SYSTEM AND METHOD FOR MANUFACTURING DISPOSABLE DIAPERS HAVING ELASTIC WAISTBAND

BACKGROUND OF THE INVENTION

1. Field of the Invention

The present invention relates to a system and method for manufacturing disposable diapers with an elastic foam waistband.

2. Description of the Prior Art

There has been a large consumer demand for disposable diapers for many years. Typically, disposable diapers are fabricated with three layers: an outer, impervious barrier layer usually of a thin plastic; an inner, porous layer of a thin cellulose fiber; and an absorbent pad extending along a portion of the space between the inner and outer layers. Disposable diapers also have been manufactured with elastic banding along the portions of the periphery which encircle the baby's legs when the diaper is worn.

Recently, there have been investigations into the use of an elastic waistband along the portion of the periphery of the diaper which encircles the child's waist during use. In one arrangement, the elastic waistband is formed with a length of thin elastic foam which is stretched and then adhered between the inner and outer layers at the predetermined waistband locations. The manufacturing technique used to stretch the lengths of elastic waistband form employs plural pins which first penetrate the ends of each waistband foam length and then stretch the length across its longitudinal direction. However, the penetration of the waistband length with the stretching pins has several potential disadvantages. First, the penetration of the waistband length forms voids which sometimes tear during stretching Second, the stretching pins must necessarily be small, and if broken during the manufacturing operation may be hidden within the diaper until used. Third, the penetration process does not lend itself to the high speed manufacturing operations necessary for the efficient production of disposable diapers.

SUMMARY OF THE INVENTION

The present invention is a system and method which provides for the high speed manufacture of disposable diapers having an elastic waistband, in which the elastic waistband is stretched during manufacture without penetration. To this end, the method of the present invention comprises the steps of providing an elongated length of a waistband material having an elastic memory, longitudinally stretching the elastic waistband length by gripping without penetrating at least one of its ends, providing a diaper layer having a predetermined portion defining a waistband area, passing the elastic waistband length and the diaper layer one with respect to the other while continuing the stretching step, and thereafter fixing the stretched elastic waistband to the diaper layer along the waistband area. In accordance with the present invention, the step of longitudinally stretching without penetration comprises pinching at least one of the ends of the elastic waistband length against a roller surface and rotating the roller surface at an outward angle with respect to the direction of travel of the waistband length in order to achieve the desired stretching. Preferably, the end of the waistband length is positively engaged in a groove of the roller surface with a continuous belt which moves across the grooved roller surface with the end of the elastic waistband length underneath the belt.

Suitably, the apparatus of the present invention comprises a pair of stretching rollers, both of which are positioned at an outward angle along the direction of waistband length travel away from a transfer service, each stretching roller having a corresponding smooth surfaced gripping belt along only a portion of the surface and defining an entry point where the gripping belt comes in contact with the corresponding roller surface and an exit point where the gripping belt leaves the corresponding stretching roller surface. A moving transfer surface is provided so as to deposit the spaced waistband lengths underneath the gripping belts and onto the stretching rollers at the entry point, and to discharge the stretched waistband lengths at the exit point and on to a moving diaper layer at the exit point. Suitably, the transfer surface has a dimension across the direction of waistband length travel which is substantially less than the dimension of the waistband length, and is approximately equal to or less than the spacing of the stretching rollers at the entry point.

The elastic waistband lengths may be cut into widths which are approximately equal to twice the desired width of a waistband length for an individual diaper, and subsequently cut longitudinally so that each waistband length forms an elastic waistband portion for two adjacent diapers.

The diaper manufactured according to the system and method of this invention thus has a length of elastic foam along a portion of the attached periphery of the inner and outer layers which define the waistband area, and which foam waistband is free of any penetrations.

DESCRIPTION OF THE DRAWINGS

FIG. 1 is a top plan view illustrating a diaper manufactured in accordance with the present invention.

FIG. 2 is a perspective view of a portion of a diaper manufactured in accordance with the present invention, and illustrating the features of the elastic waistband.

FIG. 3 is a cross-section of a portion of a continuous disposable diaper run manufactured in accordance with the present invention, illustrating how two adjacent disposable diapers are manufactured with a common disposable elastic waistband length, which is then severed in two by cutting.

DETAILED DESCRIPTION

Figure 4:
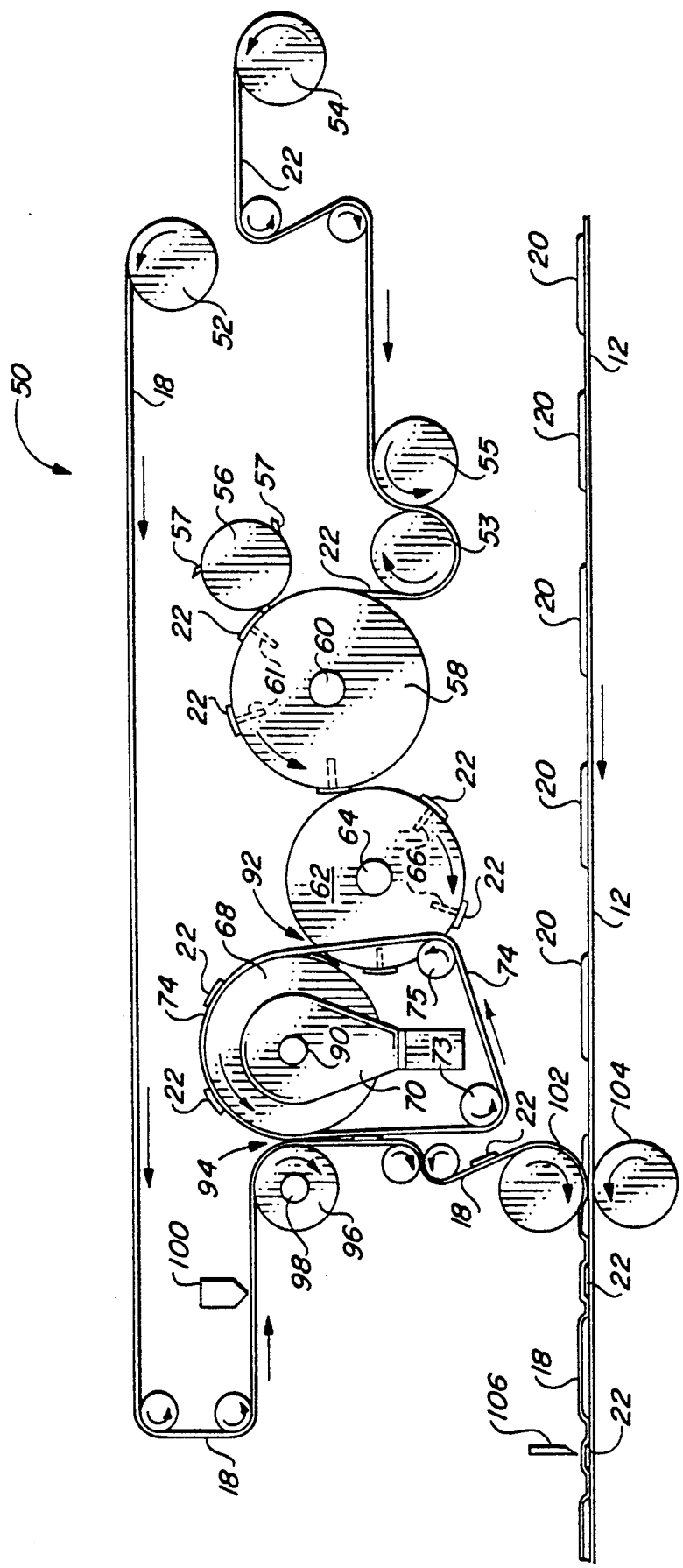
FIG. 4 is a schematic side view of a manufacturing system useful in manufacturing disposable diapers in accordance with the present invention.

A disposable diaper manufactured in accordance with the present invention will now be described with reference to FIGS. 1 and 2. The disposable diaper 10 includes a thin plastic barrier layer 12 having opposing ends 14, 16 which generally define the waistband of the diaper 10 when in use. The diaper 10 includes an inner cellulose fiber layer 18 which is generally quite porous and which easily passes liquids to an underlying padding layer 20, which is typically glued to the barrier layer 12.

In accordance with the present invention, the diaper 10 is provided with two lengths 22 of elastic foam, each positioned along one of the waistband sides 14, 16. As shown in FIG. 2, the elastic waistband lengths 22 are adhered between the inner and outer layers 12, 18 while stretched, and when permitted to return to its original configuration, form elastic folds 24 in the waistband of the diaper. The use of I0 this inexpensive elastic waistband foam 22 thus permits a snugly fitting diaper to be manufactured at a relatively low cost, while also providing a waistband moisture barrier.

The diaper includes elastic banding 26 around the curved side portions 27 which form the leg holes of the diaper when in use, and a pair of holding tabs 28.

A continuous line of manufactured disposable diapers, prior to cutting, is shown in FIG. 3 and referred to generally by the reference numeral 40. The continuous diaper line includes the inner and outer layers 12, 18 and the inserted pad 20. Additionally, as shown, a single length of elastic foam forms the elastic waistband 22 for adjacent diapers, which are then cut along a line 42 to form the elastic waistbands for two adjacent diapers.

Figure 5:
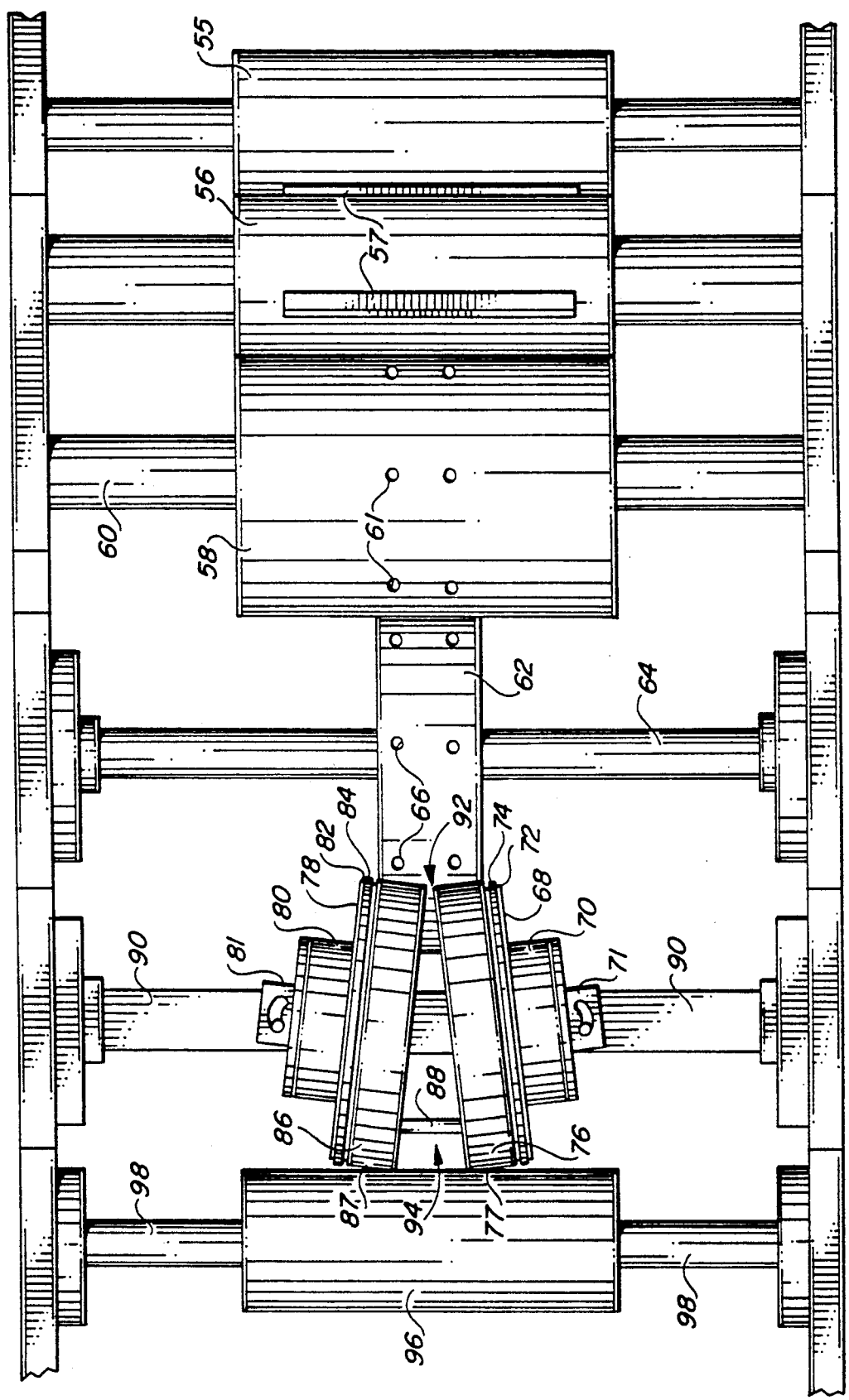
FIG. 5 is a top plan view of a portion of the apparatus shown in FIG. 4, and with the various web materials used to manufacture the diaper omitted.
Figure 6:
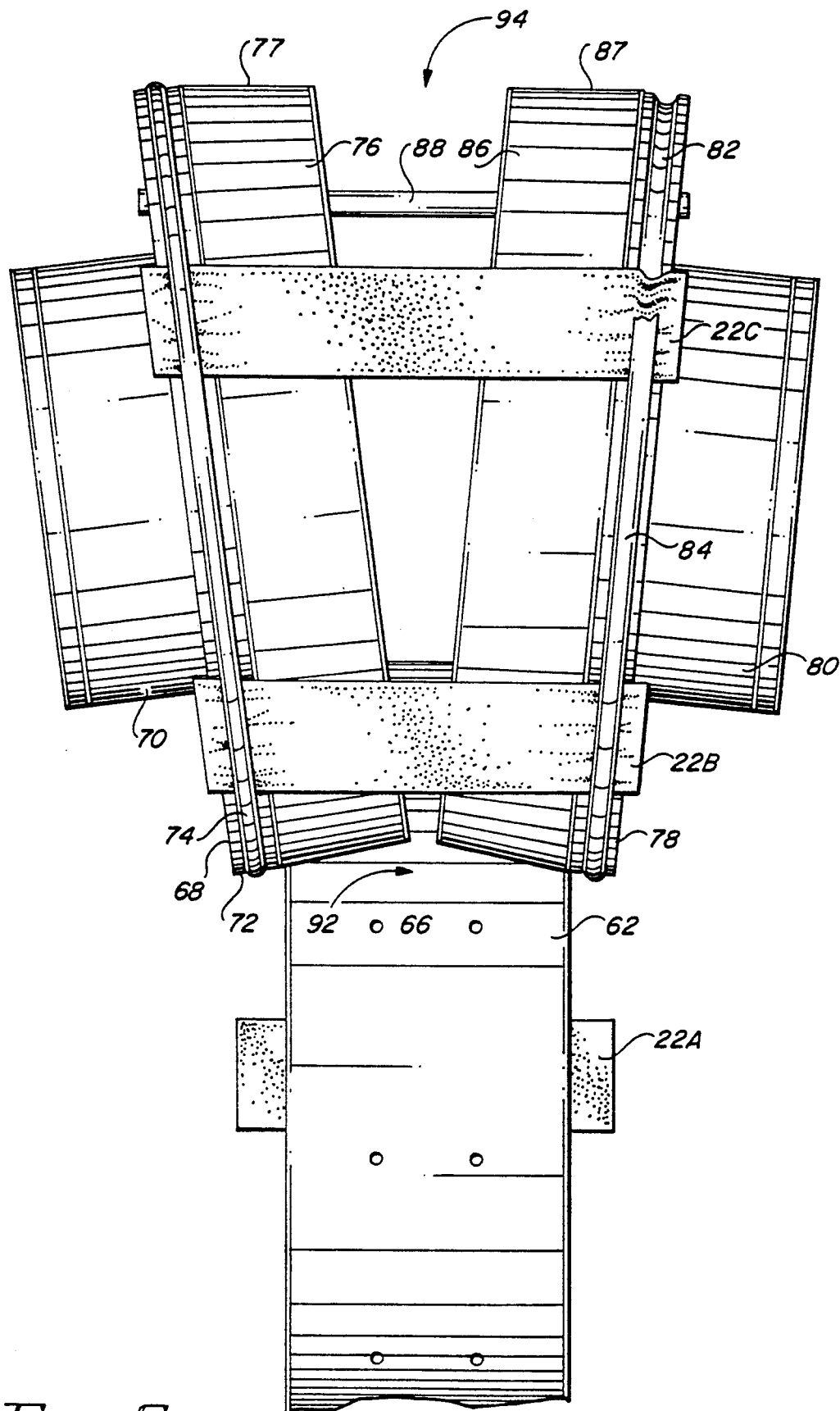
FIG. 6 is a top plan view similar to that of FIG. 5, illustrating the transfer surface and outwardly disposed stretching roller portions of the manufacturing system shown in FIGS. 4 and 5.

The system and method for manufacturing disposable diapers with elastic waistbands in accordance with the present invention without penetration of the waistband lengths will now be described with reference to FIGS. 4–6.

First noting FIG. 4, the system 50 includes webs of the working material as follows: an upper web of the cellulose inner layer 18 supported by feed roller 52; a middle web of the elastic foam waistband material 22 fed from roller 54; and a web of the plastic outer barrier layer 12, upon which are adhered the absorbent pads 20 at spaced intervals. As shown, the web of elastic foam 22 is passed through metering rollers 53, 55 into a knife roller 56 having knife blades 57 at which point the web of elastic foam is cut into individual waistband lengths 22. The foam waistband material is adhered to anvil roller 58 via vacuum and metered out to length by metering rollers 53 and 55. The knife roller 56 cuts lengths 22 of the foam, and vacuum chucks 61 on the anvil roller 58 carry the cut lengths 22 to the transfer roller 62. The anvil roller 58 is rotated via shaft 60.

At an appropriate transfer point, the individual waistband lengths are received along the surface of a transfer roller 62 which is rotated by drive shaft 64. The transfer roller 62 includes vacuum chucks 66 which hold the individual waistband length 22 across the transfer surface of the transfer roller 62, until such time as the individual waistband lengths are fed into the entry point 92 of the stretching rollers 68, 78. As is particularly shown in FIGS. 5 and 6, the crosswise dimension of the transfer surface of the transfer roller 62 is substantially less than the lengthwise dimension of each elastic waistband length 22, and is approximately equal to or less than the inner spacing between the stretching rollers 68, 78 at the entry point 92.

The construction details of the stretching rollers 68, 78 and the associated features will now be described. The stretching rollers 68, 78 are mounted on respective hubs 70, 80, each of which may be individually adjusted at an outwardly skewed angle from an entry point 92 to an exit point 94 (FIG. 4) by use of a sliding adjustment plate 71, 81. Each rotating stretching roller 68, 78 includes a corresponding peripheral groove 72, 82 across which passes a corresponding smooth surfaced gripping belt 74, 84. As shown in FIG. 4, each of the belts 74, 84 pass across a pair of lower rollers, including rollers 73, 75 which are associated with gripping belt 74, the belts dimensioned to fit within the corresponding peripheral groove 72, 82. As shown in FIG. 4, each gripping belt approaches the periphery of the corresponding roller 68, 78 at the entry point 92, with the transfer surface of the transfer roller 62 extending inside of the space between the two gripping belts 74, 84. The rollers associated with the gripping belts 74 and 84, including rollers 73 and 75, are positioned outwardly so that the ends of the waistband lengths may pass underneath the belts as each length approaches the entry point 92. Each stretching roller 68, 78 includes an inwardly extending member 76, 86 each of which defines a respective anvil surface 77, 87 for pressing the discharged stretched elastic waistband lengths 22 against a pressure roller 96 across which passes the web of inner layer 18, after glue or a like adhesive is deposited via glue gun 100 at predetermined intervals along the web of inner layer 18. Thus, as shown in FIG. 4, the stretched elastic waistband lengths 22 are adhered to the web 18, and are subsequently passed into combining rollers 102, 104 for application to the web of inner layer 12 and absorbent pad 20. The combined web is then cut at 106 in the manner described above with reference to FIG. 3.

The manner in which the elastic waistband lengths are continuously stretched in a high speed operation will now be described with reference to FIG. 6. As there shown, the transfer surface of the transfer roller 62 is substantially narrower than the lengthwise dimension of each waistband length, including waistband length 22A which is depicted on the underneath side of the transfer roller 62. As each individual waistband length passes between the gripping belts 74, 84 and moves toward the entry point 92, the gripping belts come in contact with the respective ends of each waistband length; simultaneously, the vacuum associated with vacuum chucks 66 along the transfer roller 62 may be discontinued in a conventional manner, thereby permitting the gripping belts to pinch the respective end of the waistband length (including waistband lengths 22B and 22C in FIG. 6) into the peripheral groove of the respective roller 68, 78 (in FIG. 6, note curvature of waistband length 22C, where a portion of the gripping belt 84 is cut away). Continuous rotation of the stretching rollers 68, 78 then permits each stretched waistband length 22 to be discharged at the exit point 94 and simultaneously be adhered in the stretched condition to the predetermined areas where glue has been applied at 100 onto the web of the inner layer 18.

It will be appreciated by those skilled in the art that the continuous stretching process provided for by the non-penetrating roller system described above permits the high speed manufacture of disposable diapers having stretched elastic waistband lengths without penetrating the waistband lengths during the manufacturing operation. It will also be appreciated by those skilled in the art that numerous modifications and changes in detail may be made without departing from the spirit and scope of the present invention.

I claim:

1. A method for making an elastic waistband for disposable diapers, comprising the steps of:
providing an elongated length of a waistband material having an elastic memory;
longitudinally stretching the elastic waistband length by pinching without penetrating at least one of the ends of the elastic waistband length against a roller surface, and rotating the roller surface at an outwardly skewed angle;

providing a diaper layer having a predetermined portion defining a waistband area;

passing the elastic waistband length and the diaper layer one with respect to the other while continuing the stretching step; and fixing the stretched elastic waistband length to the diaper layer along the waistband area.

2. The method recited in claim 1 wherein the pinching step comprises pressing a continuous belt against the roller surfacee with said at least one of the ends of the elastic waistband length between the belt and the roller surface.

3. The method recited in claim 2 further comprising the step of positively engaging said at least one of the ends of the waistband length with the roller surface.

4. The method recited in claim 3 wherein the positively engaging step comprises fitting a groove in the roller surface, the grooved roller surface dimensioned to receive the continuous belt, and with the belt engaging in the groove.

5. The method recited in claim 4 wherein the elastic waistband length comprises an open-cell elastic form.

6. The method recited in claim 1 wherein the longitudinally stretching step comprises stretching the elastic waistband length continuously while moving along an arcuate path by pinching without penetrating both of the ends of the elastic waistband length, and continuously pulling the ends laterally across the arcuate path.

7. A method for making elastic waistbands for disposable diapers, comprising the steps of:

passing a continuous web of an elastic waistband material having an elastic memory to a cutting means and cutting the web into a plurality of waistband lengths;

continuously transferring the waistband lengths from the cutting means to a pair of spaced, continuously rotating rollers;

longitudinally stretching each elastic waistband length by pinching without penetrating each end of each waistband length against a corresponding one of the spaced rollers, and then stretching each waistband length during rotation of the rollers at outwardly skewed angles;

providing a diaper layer predetermined portions defining a waistband area;

passing the stretched elastic waistband lengths and the diaper layer one with respect to the other while continuing the stretching step; and fixing the stretched elastic waistband lengths to the diaper layer along the waistband areas, respectively.

8. The method recited in claim 7 wherein the stretching step further comprises pressing a continuous belt against each roller surface with the ends of each elastic waistband length between the belt and the corresponding roller surface.

9. The method recited in claim 8 wherein the steps of pinching without penetrating the ends of the waistband lengths with the corresponding roller surface comprises the step of fitting a groove in each roller surface, each grooved roller surface dimensioned to receive the corresponding continuous belt, and with the belt engaging in the groove.

10. The method recited in claim 8 wherein the step of passing the elastic waistband lengths and the diaper layer comprises the steps of:

passing the diaper layer as a continuous web in proximity to the spaced stretching rollers;

transferring the stretched waistband lengths at predetermined intervals to the diaper layer.

11. The method recited in claim 10 further comprising conducting the step of transferring the waistband lengths to the diaper layer at a point where each continuous belt leaves the corresponding stretching roller.

12. A method for the continuous manufacture of a disposable diapers having a stretchable foam waistband with an elastic memory, comprising the steps of:

spacing the waistband lengths along a moving transfer surface;

moving the transfer surface into proximity to a pair of spaced, rotating stretching rollers;

passing a smooth surface gripping belt across only a portion of the surface of each stretching roller, each belt having an entry point and an exit point with respect to the corresponding roller surface, each belt further engaging an end of each length of waistband material near the entry point and pinching the end against the corresponding stretching roller during rotation between the entry and exit points;

positioning the stretching rollers at an outward angle along the direction of waistband length travel away from the transfer surface, whereby rotation of the spaced rollers at the outward angle effectuates the stretching of each elastic waistband length between the entry and exit points; and depositing the waistband lengths at the exit point along spaced intervals on a moving web of a disposable diaper layer.

13. The method recited in claim 12 wherein the depositing step comprises adhering each waistband length as it passes through the exit point of the gripping belts.

14. The method recited in claim 12 further comprising the step of controlling the spacing of the waistband lengths along the diaper layer by controlling the speed of movement of the transfer surface.

15. The method recited in claim 12 further comprising the step of spacing the stretching rollers along the outward angle so that the roller spacing is narrow adjacent the entry point and its widest adjacent the exit point.

16. The method recited in claim 12 wherein the period of rotation of the stretching roller is between the entry and exit points is approximately 180° of rotation.

17. The method recited in claim 12 further comprising, before the step of spacing the waistband lengths along the transfer surface, the step of passing a continuous web of the elastic waistband material to a cutting means and cutting the web into a plurality of the waistband lengths, and continuously transferring the waistband lengths from the cutting means to the transfer surface.

18. The method recited in claim 12 wherein the depositing step comprises the step of:

applying an adhesive to the moving web of diaper layer at the location of the spaced intervals;

sequentially removing the stretched waistband lengths from the stretching rollers at the exit point and simultaneously depositing each length on an area of the applied adhesive along the spaced intervals; and during the removing step, pressing each waistband length against the diaper layer.

19. The method recited in claim 12 wherein each deposited waistband length has a width which is approximately twice the desired dimension of web material for each individual diaper, the method comprising the step of cutting the waistband length and the diaper barrier layer lengthwise, so that the waistband length forms a stretchable waistband for two adjacent disposable diapers.

20. A method for stretching lengths of elastic material for use as waisbands for disposable diapers, comprising the steps of:
   providing a pair of spaced stretching rollers each having a gripping surface, the stretching rollers defining an entry point in which the dimension between the stretching rollers is approximately equal to the lengthwise dimension of an unstretched elastic waistband length which is to be stretched, the stretching rollers also defining an exit point in which the dimension between the stretching rollers is approximately equal to the lengthwise dimension of the elastic waist band length when in the desired stretched condition;
   moving the stretching rollers in a direction from the entry point to the exit point;
   continuously passing plural elastic waistband lengths into the entry point;
   gripping without penetrating each end of each elastic waistband length across the surface of one of the stretching rollers; and thereafter
   discharging each elastic waistband length in a stretched condition at the exit point.

21. The method recited in claim 20 wherein the gripping step comprises passing a continuous belt along each stretching roller with one end of each elastic waistband length pinched between the belt and the surface of the corresponding stretching roller.

22. The method recited in claim 21 further comprising the step of providing the belt with a smooth surface.

23. The method recited in claim 22 further comprising the step of fitting a groove along the surface of each stretching roller, the groove dimensioned to receive a corresponding gripping belt.

24. The method recited in claim 20 wherein the elastic waistband lengths comprise a foam having an elastic memory.

25. Apparatus for making disposable diapers having an elastic waistband, comprising:
   means for longitudinally stretching an elongated length of waistband material having an elastic memory by gripping without penetrating at least one of its ends, the longitudinal stretching means including a roller surface rotating at an outwardly skewed angle and means for pinching without penetrating at least one of the ends of the elastic waistband length against the roller surface; and
   means for passing the elastic waistband length and a diaper layer having a predetermined portion defining a waistband area one with respect to the other and for receiving the stretched elastic waistband length while in the stretched condition and for fixing the stretched elastic waistband to the diaper layer along the waistband area.

26. The apparatus recited in claim 25 wherein the pinching means comprises a continuous belt across the roller surface with the end of the elastic waistband length, and further comprising means for feeding the waistband lengths between the belt and the roller surface.

27. The apparatus recited in claim 26 further comprising means for positively engaging the end of the waistband length with the roller surface.

28. The apparatus recited in claim 27 wherein the positively engaging means comprises a groove in the roller surface, the grooved roller surface dimensioned to receive the continuous belt.

29. Apparatus for the continuous manufacture of disposable diapers having a stretchable foam waistband with an elastic memory comprising:
   a moving transfer surface;
   means for spacing a plurality of individual waistband lengths along the moving transfer surface;
   a pair of spaced, rotating stretching rollers, the stretching rollers being spaced at an outward angle along the direction of waistband length travel away from the transfer surface;
   means for moving the transfer surface into proximity to the pair of stretching rollers;
   two smoothed surface gripping belts positioned across only a portion of the surface of a corresponding stretching roller, each belt having an entry point and an exit point to the corresponding roller surface, each belt for engaging an end of the length of waistband material near the entry point so as to pinch the end of the waistband material against the corresponding stretching roller during rotation between the entry and exit points; and
   the stretching rollers defining means for depositing the stretched waistband lengths at spaced intervals along a moving web of a disposable diaper layer.

30. The apparatus recited in claim 29 wherein the depositing means further comprises:
   means for applying an adhesive to the moving web of the diaper layer at the location of the spaced interval;
   means for sequentially removing the stretched waistband lengths from the stretching rollers at the exit point and depositing each length on the applied adhesive along the spaced intervals; and
   means for pressing the diaper layer and the stretched waistband length together along the direction of travel at the exit point.

31. Apparatus for stretching lengths of elastic material for use as waistbands for disposable diapers, comprising:
   a pair of spaced stretching rollers each having a gripping surface, the stretching rollers defining an entry point haivng a first dimension between the gripping surfaces of the stretching rollers, the stretching rollers also defining an exit point having a second dimension between the gripping surfaces of the stretching rollers which is substantially greater than the first dimension and which is approximately equal of an elastic waistband length when in the desired stretched condition;
   means for moving the stretching rollers in a direction from the entry point to the exit point;
   means for continuously passing plural elastic waistband lengths into the entry point;
   means for pinching without penetrating each end of each elastic waistband length across the surface of one of the stretching rollers, respectively, from said entry point to said exit point.

32. The apparatus recited in claim 31 wherein the means for gripping comprises a continuous belt along each stretching roller, with one end of each elastic waistband length being pinched between the belt and the surface of the corresponding stretching roller.

* * * * *